United States Patent [19]
Matyus et al.

[11] Patent Number: 5,395,934
[45] Date of Patent: Mar. 7, 1995

[54] 3(2H)-PYRIDAZINONE DERIVATIVES AND PROCESS FOR THE PREPARATION THEREOF

[75] Inventors: Peter Matyus; Klara Czako; Ildiko Varga, all of Budapest; Andrea Jednakovics, Szentendre; Agnes Papp, Budapest; Ilona Bodi, Eger; Gyorgy Rabloczky, Budapest; Andras Varro, Budapest; Laszlo Jaszlits, Budapest; Aniko Miklos, Budapest; Luca Levay, Budapest; Gvorgy Schmidt, Budapest; Marton Fekete, Budapest; Maria Kurthy, Budapest; Katalin Szemeredi, Budakalasz; Erzsebet Zara, Budapest, all of Hungary

[73] Assignee: EGIS Gyogyszergyar, Budapest, Hungary

[21] Appl. No.: 995,295

[22] Filed: Dec. 21, 1992

[30] Foreign Application Priority Data

Dec. 20, 1991 [HU] Hungary ............... 40 57/91

[51] Int. Cl.$^6$ ............................ C07D 237/10
[52] U.S. Cl. ........................ 544/241; 540/574; 544/114; 544/238; 544/239; 544/383; 544/403
[58] Field of Search ............... 544/239, 241, 238; 514/247, 252

[56] References Cited

U.S. PATENT DOCUMENTS

| | | | |
|---|---|---|---|
| 4,088,764 | 5/1978 | Raabe | 544/238 |
| 4,532,239 | 7/1985 | Raabe et al. | 544/239 |
| 4,783,462 | 11/1988 | Mutsukado et al. | 544/239 |
| 4,992,433 | 2/1991 | Stokbroekx | 514/212 |
| 5,034,391 | 7/1991 | Blaschke | 544/238 |

Primary Examiner—Donald G. Daus
Attorney, Agent, or Firm—Beveridge, DeGrandi, Weilacher & Young

[57] ABSTRACT

Racemic or optically active new 3(2H)-pyridazinone derivatives, a process for the preparation thereof, pharmaceutical compositions comprising the same, to the use of the said 3(2H)-pyridazinone derivatives for the treatment of diseases and for the preparation of pharmaceutical compositions suitable for the treatment of diseases.

The new 3(2H)-pyridazinone derivatives according to the invention correspond to the general formula (I),

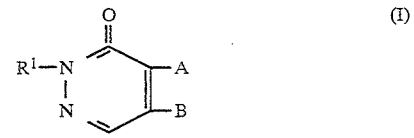

5 Claims, 1 Drawing Sheet

Figure 1

3(2H)-PYRIDAZINONE DERIVATIVES AND PROCESS FOR THE PREPARATION THEREOF

This invention relates to racemic or optically active new 3(2H)-pyridazinone derivatives, a process for the preparation thereof, pharmaceutical compositions comprising the same, to the use of the said 3(2H)-pyridazinone derivatives for the treatment of diseases and for the preparation of pharmaceutical compositions suitable for the treatment of diseases.

According to an aspect of the present invention there are provided racemic or optically active new 3(2H)-pyridazinone derivatives of the general formula (I), wherein
R$^1$ represents hydrogen; phenyl; methyl optionally carrying a benzyloxy substituent; C$_{1-4}$ alkyl optionally carrying a substituent of the formula R$^8$R$^9$N—, wherein R$^8$ and R$^9$ are independently C$_{1-4}$ alkyl, or R$^8$ and R$^9$ form, together with the adjacent nitrogen atom, a 6-membered heterocyclic group optionally containing an oxygen atom or a group of the formula R$^{10}$N—, wherein R$^{10}$ stands for C$_{1-4}$ alkyl optionally carrying a phenoxy substituent, or C$_{3-5}$ alkenyl carrying a phenyl substituent; furthermore said C$_{1-4}$ alkyl is optionally substituted by a phenyl carrying a methoxy or a methanesulfonylamino substituent; or C$_{3-5}$ alkenyl optionally carrying a phenyl or halophenyl group;

A and B stand for hydrogen, halogen or a group of the general formula (II), wherein
R$^2$ and R$^3$ are independently hydrogen or C$_{1-4}$ alkyl, or together with the adjacent —N—(CH$_2$)$_n$N— group form a piperazine or homopiperazine ring;
R$^4$ represents hydrogen, C$_{1-4}$ alkyl or phenyl,
R$^5$, R$^6$ and R$^7$ each stand for hydrogen, C$_{1-4}$ alkoxy or amino optionally carrying a methanesulfonyl substituent;
X is a single valency bond, an oxygen atom or a group of the formula —CH═CH—;
m is 0 or 1, and
n is 2 or 3,
with the proviso that A and B are always different, and if one of A and B is hydrogen or halogen, the other stands for a group of the general formula (II), and acid addition salts thereof.

The invention encompasses all of the tautomeric forms of the compounds of the general formula (I).

The compounds according to the present invention possess valuable antiarrhythmic effect.

The terms "C$_{1-4}$ alkyl" and "C$_{1-4}$ alkyl" used throughout the specification relate to straight or branched chained saturated aliphatic hydrocarbon groups having the given number of carbon atoms, e.g. methyl, ethyl, propyl, isopropyl, n-butyl, i-butyl etc. As "C$_{3-5}$ alkenyl groups" straight or branched chained alkenyl groups are mentioned, e.g. allyl, 2-methylallyl, 1-propenyl, 2-propenyl, 1-butenyl, etc. The term "halogen atom" encompasses all the four halogen atoms (fluorine, chlorine, bromine and iodine).

The compounds wherein R$^1$ stands for hydrogen, methyl or C$_{1-4}$ alkyl optionally substituted by a diethylamino group, A represents chlorine or bromine being attached to the pyridazinone ring in position 4 and B denotes an optionally substituted 1-(3-phenyl-2-propen-1-yl)-piperazino group being attached to the pyridazinone ring in position 5 belong to a preferred group of the compounds of the general formula (I).

The compounds wherein R$^1$ represents hydrogen or C$_{1-4}$ alkyl substituted by a diethylamino or 1-(2-phenoxyethyl)-piperazino group, A denotes halogen, B is a group of the general formula (II), wherein R$^2$, R$^4$ and R$^5$ represent hydrogen, R$^3$ stands for methyl, R$^6$ and R$^7$ are methoxy, X is a single valency bond, m is 1 and n is 3, furthermore A is attached to the pyridazinone ring in position 5 and B is attached to the same ring in position 4, belong to another preferred group of the compounds of the general formula (I).

Particularly preferred representatives of the compounds of the general formula (I) are the following derivatives:
5-chloro-4-{3-[N-[2-(3,4-dimethoxyphenyl)-ethyl]-N-methylamino]-propylamino}-3(2H)-pyridazinone,
4-chloro-2-[2-(N,N-diethylamino)-ethyl]-5-{4-(3-phenyl-2-propenyl)-1-piperazinyl}-3(2H)-pyridazinone,
5-chloro-4-{3-[N-[2-(3,4-dimethoxyphenyl)-ethyl]-N-methylamino]-propylamino}-2-[2-morpholinoethyl]-3(2H)-pyridazinone,
5-chloro-2-[2-(N,N-diethylamino)-ethyl]-4-{3N-[2-(3,4-dimethoxyphenyl)-ethyl]-N-methylamino]-propylamino}-3(2H)-pyridazinone,
4-{3-[N-[2-(3,4-dimethoxyphenyl)-ethyl]-N-methylamino]-propylamino}-3(2H)-pyridazinone,
5-chloro-4-{3-[N-[2-(3,4-dimethoxyphenyl)-ethyl]-N-methylamino]-propylamino}-2-{4-[(methylsulfonyl)-amino]-benzyl}-3(2H)-pyridazinone,
5-chloro-4-{3-[N2-[4-[(methylsulfonyl)-amino]-phenoxy]-ethyl]-N-methylamino]-propylamino}-3(2H)-pyridazinone, and pharmaceutically acceptable acid addition salts thereof.

The new 3(2H)-pyridazinones according to the invention belong to a group of compounds which is so far less known in the art.

Japanese patent application No. 78-12,880 describes some 2-alkyl, 2-alkenyl, 2-aralkyl and 2-aryl derivatives of 5- and 4-(2-hydroxyethyl)-amino-3(2H)-pyridazinone compounds structurally similar to the compounds according to the invention, which serve as intermediates for the preparation of pyridazino-[4,5-b][1,4]-oxazines exerting antiinflammatory, antidepressant and analgesic activities.

Czechoslovakian patent specification No. 223,432 relates to 2-(C$_{1-3}$) alkyl, 2-cycloalkyl, 2-aryl and 2-(optionally substituted) aralkyl-5-chloro-3(2H)-pyridazinones containing an alkyl, alkoxyalkyl, cycloalkylamino, pyrrolidino or piperidino group in position 4.

French patent specification No. 2,124,164 provides 2-phenyl-6-chloro (or methoxy)-4-[4-(ω-benzoylalkyl)-

1-piperazinyl]-3(2H)-pyridazinones possessing analgesic, sedative and hypotensive properties.

Published German patent application No. 3,902,316A relates to piperazinyl-(alkylamino)-pyridazinone derivatives having alpha-adrenoceptor blocking activity, wherein—contrary to the compounds according to the invention—the piperazine and pyridazinone rings are not attached to one another directly, but via an alkyleneamino chain.

Published European patent application No. 320,032A describes 3-(phenylamino-alkyl)-amino and 3-[4-(phenoxyalkyl)-piperazino]-pyridazines, furthermore the 6-hydroxy and 6-chloro derivatives thereof. These compounds possess antiviral activity.

Published European patent specification No. 54,946 provides 4-chloro-5-[2-(3-phenoxy-2-hydroxy-propylamino)-ethyl]-amino-3(2H)-pyridazinone derivatives structurally different from the 3(2H)-pyridazinones according to the invention. Although alpha- and beta-receptor-blocking, antiarrhythmic and antihypertensive effects are attributed to the described compounds, only the antihypertensive activity is proved by test results.

According to a further aspect of the present invention there is provided a process for the preparation of racemic or optically active 3(2H)-pyridazinone derivatives of the general formula (I), which comprises a) for the preparation of the compounds of the general formula (I), wherein one of A and B is other than hydrogen and $R^1$ is as stated above, reacting a compound of the general formula (III), wherein $R^1$ is as stated above and Hal represents halogen, with an amine of the general formula (IV), wherein $R^2$, $R^3$, $R^4$, $R^5$, $R^6$, $R^7$, X, m and n have the same meaning as above; or b) for the preparation of the compounds of general formula (I), wherein $R^1$ is other than hydrogen or phenyl, A, B and $R^3$ are other than hydrogen and $R^2$, $R^4$, $R^5$, $R^6$, $R^7$, X, m and n are as defined above, reacting a compound of the general formula (I), wherein $R^1$ is hydrogen and $R^3$ is other than hydrogen and $R^2$, $R^4$, $R^5$, $R^6$, $R^7$, X, m and n are as defined in the introductory part, with a compound of the general formula $R^1Z$, wherein $R^1$ is as defined in the introductory part except that it may not stand for hydrogen or phenyl, and Z is a leaving group; or c) for the preparation of the compounds of the general formula (I), wherein A and B are as defined in the introductory part, $R^2$ and $R^3$ are the same or different and represent hydrogen or $C_{1-4}$ alkyl and $R^1$, $R^4$, $R^5$, $R^6$, $R^7$, X, m and n are as defined in the introductory part, reacting a compound of the general formula (V), wherein $R^1$ is as defined in the introductory part, C and D are hydrogen or halogen atom or a group of the general formula (VI), wherein $R^2$ is hydrogen or $C_{1-4}$ alkyl, Z stands for a leaving group and n is as defined in the introductory part, with the proviso that one of C and D is always hydrogen or halogen, and with the further proviso that if one of them is hydrogen or halogen, the other is a group of the general formula (VI), with an amine of the general formula (VII), wherein $R^3$ is hydrogen or $C_{1-4}$ alkyl, $R^4$, $R^5$, $R^6$, $R^7$, X and m are as stated in the introductory part; or d) for the preparation of the compounds of the general formula (I), wherein $R^1$ is other than hydrogen and A and B are as defined in the introductory part, reacting a compound of the general formula (VIII), wherein $R^1$ and n are as defined in the introductory part and Y represents hydrogen or halogen, with the proviso that one of Y and the —$N(R^2)$—$(CH_2)_n$—$NH(R^3)$ group is always attached to the pyridazinone ring in position 4 and the other is attached to the same ring in position 5, with a compound of the general formula (IX), wherein $R^4$, $R^5$, $R^6$, $R^7$, X and m are as defined in the introductory part and Z is a leaving group; or e) for the preparation of the compounds of the general formula (I), wherein $R^1$ is hydrogen and A and B are as defined in the introductory part, treating a compound of the general formula (I), wherein $R^1$ stands for a benzyloxymethyl group and A and B are as stated in the introductory part, with boron tribromide; or f) for the preparation of the compounds of the general formula (I), wherein one of A and B is hydrogen and $R^1$ is as defined in the introductory part, dehalogenating a compound of the general formula (I) obtained according to any of process variants a)–e), wherein $R^1$ is as defined in the introductory part, A and B represent halogen or a group of the general formula (II), with the proviso that if one of A and B is halogen, the other represents a group of the general formula (II), and, if desired, converting a compound of the general formula (I) obtained according to process variants a)–f) into an acid-addition salt thereof and/or separating the optically active isomers.

According to a preferred embodiment of process variant a) for the preparation of compounds of the general formula (I), wherein A stands for a group of the general formula (II) and B is as stated in the introductory part, a 4,5-dihalo-3(2H)-pyridazinone derivative of the general formula (III) is reacted with an amine of the general formula (IV) in an apolar solvent, such as dioxane or toluene, at a temperature between 50° C. and the boiling point of the solvent. The amine is applied in a twofold–tenfold excess related to one mole of the compound of the general formula (III).

According to a preferred embodiment of process variant a) for the preparation of compounds of the general formula (I), wherein B is a group of the general formula (II) and A is as defined in the introductory part, a compound of the general formula (III) is reacted with an amine of the general formula (IV) in a polar solvent, e.g. ethanol or a mixture of ethanol and water, at a temperature between 50° C. and the boiling point of the solvent. The amine is applied in a twofold–tenfold excess calculated on one mole of the compound of the general formula (III).

According to a preferred embodiment of process variant b) a compound of the general formula (I), wherein $R^1$ represents hydrogen, is reacted with a compound of the general formula $R^1Z$, wherein Z is preferably chlorine or bromine, in an aprotic solvent, preferably in a dipolar-aprotic solvent, such as dimethylformamide, in the presence of an acid-binding agent, such as potassium carbonate, at a temperature between 25° C. and the boiling point of the solvent.

According to a preferred embodiment of process variant c) a compound of the general formula (V) is reacted with an amine of the general formula (VII) either without using any solvent or in a solvent, preferably in a dipolar-aprotic solvent, such as dimethylformamide, at a temperature between 50° C. and 150° C. The amine is used in a twofold–tenfold excess related to one mole of the compound of the general formula (V).

According to a preferred embodiment of process variant d) a compound of the general formula (VIII) is reacted with a compound of the general formula (IX), wherein Z is preferably chlorine or bromine, without using any solvent or in a solvent, preferably in a dipolar-aprotic solvent such as dimethylformamide, optionally in the presence of an acid-binding agent such as an organic or inorganic base, at a temperature between 25° C. and 120° C.

According to a preferred embodiment of process variant e) a compound of the general formula (I), wherein $R^1$ stands for a benzyloxymethyl group, is reacted with boron tribromide in a solvent inert towards the reactants, such as benzene or toluene, at room temperature.

According to a preferred embodiment of process variant f) a compound of the general formula (I), wherein A and B are other than hydrogen, is treated either with gaseous hydrogen or with a hydrogen donator in the presence of a catalyst suitable for dehalogenation, such as palladium on activated carbon, and optionally in the presence of an acid-binding agent, preferably an inorganic base, such as ammonia, under atmospheric pressure.

BRIEF DESCRIPTION OF THE DRAWINGS

The present invention will be further understood with reference to FIG. 1 which shows the duration (s/min) of the compound of example 1, Sotalol and a control in an in vivo reperfusion arrhythmia model.

The reaction mixture obtained according to any of the above process variants can be worked up by methods known per se, e.g. the excess of the reagent and/or solvent is removed (optionally in vacuo) and the residue is extracted and/or subjected to chromatography and-/or crystallization. The thus-obtained compound of the general formula (I) is optionally purified, e.g. by chromatography and/or recrystallization, furthermore—if it is possible and desired—it can be converted into acid-addition salts, which can be—if necessary—purified by recrystallization.

The compounds of the general formula (I) containing a strongly basic group can be converted into acid-addition salts. For this purpose the base is dissolved in an appropriate solvent, and an appropriate acid or a solution thereof in an appropriate solvent is added to it under stirring. The product thus obtained is separated by filtration or by crystallization succeeding the evaporation of the solvent and optionally purified e.g. by recrystallization. As acid organic or inorganic acids, preferably pharmaceutically acceptable acids, e.g. sulfuric acid, hydrogen chloride, fumaric or tartaric acid can be used. As solvent e.g. alcohols, esters, ethers and/or ketones may be used. The salt formation is carried out at a temperature between 0° C. and 80° C., in case of mineral acids preferably between 0° C. and 20° C., in case of organic acids preferably at a temperature between 50° C. and 80° C.

The compounds of the general formula (I), wherein $R^1$ and/or $R^2$ stand(s) for hydrogen, may exist in further tautomeric forms, too. These compounds also belong to the scope of the present invention.

The compounds of the general formula (I), wherein $R^4$ is other than hydrogen and/or the substituents $R^1$, $R^2$ and/or $R^3$ contain one or more centre(s) of asymmetry, may exist in optically active forms, too. The present invention encompasses both the racemic and the optically active forms of the compounds of the general formula (I).

Some of the compounds of the general formula (III) used as starting substances for variant a) are known in the art [e.g. J. Am. Chem. Soc. 75, 1909 (1953); Bull. Chem. Soc. France 1964, 2124; J. Heterocyclic Chem. 21, 481 (1984); Farmaco Ed. Sci. 32, 239 (1984); Chem. Pharm. Bull. 18, 147 (1970)]. Those compounds of the general formula (III) which have not been described so far in the literature can be prepared by analogous methods. Thus, the compounds of the general formula (III), wherein $R^1$ represents alkenyl carrying an optionally substituted phenyl substituent or alkyl carrying a 4-substituted 1-piperazinyl substituent can be produced by reacting a 4,5-dihalo-3(2H)-pyridazinone with an appropriate reagent of the general formula R$^1$Z, wherein Z is a leaving group, e.g. halogen. The majority of the reagents of the general formula R$^1$Z used for the reaction according to the invention is known in the art [e.g. J. Chem. Soc. 1940, 1266; ibid. 1961, 2516; J. Chem. Soc. B 1966, 590; J. Am. Chem. Soc. 83, 3846 (1961); Chem. Ber. 30, 810; Chem. Pharm. Bull. 25, 1811 (1977)], the other compounds of the general formula R$^1$Z can be produced by analogous methods. The compounds of the general formula (III) wherein R$^1$ denotes 4-(methanesulfonyl-amino)-benzyl can be produced from the compounds containing 4-nitrobenzyl as substituent R$^1$.

Some of the 1,2-ethanediamine and 1,3-propanediamine derivatives and 1-substituted piperazines of the general formula (IV) used for process variant a) as starting substances are known in the art [e.g. European patent specification No. 344,577; Belgian patent specification No. 523,902; J. Med. Chem. 11, 804 (1968)]. The new compounds of the general formula (IV) can be prepared by analogous methods. The 2-[4-[(methanesulfonylamino)-phenoxy]-ethyl chloride and the precursors thereof necessary for the preparation of 1-[2-[4-(methanesulfonylamino)-phenoxy]-ethyl]-piperazine can be produced as described in European patent specification No. 245,997 and Belgian patent specification No. 797,623.

The preparation of the new starting substances used for process variant a) is illustrated hereinafter under the title "Preparation of the starting substances" (points 1 and 2).

The alkylating agents of the general formula R$^1$Z used as starting substances for process variant b) are known in the art (see above), or can be prepared by analogous methods.

The synthesis of the new 3(2H)-pyridazinone derivatives used as starting substances for process variant c) is specified hereinafter under the title "Preparation of the starting substances" (point 3). The preparation of the amines of the general formula (VII) is known in the literature [Chem. Ber. 31, 1195; J. Am. Chem. Soc. 62, 922 (1940)].

The preparation of the compounds of the general formula (VIII) used as starting substances for process variant d) is shown hereinafter under the title "Preparation of the starting substances" (point 4).

The compounds of the general formula (I) possess valuable pharmaceutical properties. More specifically they exhibit an excellent antiarrhythmic activity.

In the therapy of rhythmic disturbances afflicting a considerable part of the population medicinal treatment is the most wide-spread method. Sudden cardiac death representing the leading cause of death in a great number of countries of the world may also be attributed to antiarrhythmia: chronic ventricular tachycardia and/or fibrillation. Against these forms of arrhythmiae, however, only the compounds belonging to class III [see: Williams Vaughan's classification of the antiarrhythmic agents, J. Clin. Pharmacol. 24, 129 (1989)] are effective due to the mechanism of their activity, and only a few of these compounds are available in the commerce. The ingredients belonging to class I representing the majority of the commercially available antiarrhythmic agents are, at the same time, practically inactive. That is why there is a great demand for new and reliable antiarrhythmics belonging to class III of the above classification.

Surprisingly it has been found that the new 3(2H)-pyridazinones of the general formula (I) according to the invention, when subjected to in vitro cellular electrophysiological experiments, cause a considerable prolongation of the duration of action potential (APD$_{90}$) characteristic of the antiarrhythmics belonging to class III. Besides, they have proved to possess excellent antiarrhythmic activity in various in vivo tests. Thus, the compounds of the general formula (I) according to the invention can be used either for the treatment or for the prophylaxis of several types of ventricular and supraventricular arrhythmiae, such as auricular and ventricular fibrillations.

The activity of the compounds of the general formula (I) is shown by the following in vitro electrophysiological experiments and in vivo induced arrhythmia models.

I. Intracellular electrophysiological studies on isolated canine Purkinje fibres: study on the characteristics and duration of the action potential Mongrel dogs of both sexes, weighing 8–22 kg, were anaesthetized with intravenously administered sodium pentobarbital, 30 mg/kg (Nembutal$^R$). The superficial Purkinje fibres were excised from the heart and placed in plastic organ bath containing Tyrode's solution (147.0 mM of Na$^+$, 4.0 mM of K$^+$, 133.3 mM of Cl$^-$, 2.0 mM of Ca$^{2+}$, 22.0 mM of HCO$_3^-$, 0.9 mM of H$_2$PO$_4^-$, 5.0 mM of glucose) The perfusate (Tyrode's solution) was gassed with a mixture of 95% of CO$_2$ and 5% of O$_2$. Temperature of the organ hath was 37.0°±0.5° C., pH=7.3±0.5. Purkinje fibres were incubated for 1–2 hours in order to avoid spontaneous changes in the duration of action potential, which were observed often for a short period after the preparation was completed. Conventional glass microelectrode method was used to measure intracellular action potentials. The electrodes were filled with 3M KCl solution, resistance was 5–15 Mohm. Microelectrodes were connected to a high input resistance capacity-neutralizing amplifier through Ag—AgCl connection. Another electrode was placed in the organ bath as a reference electrode. Maximum rate of depolarization (V$_{max}$) was measured by an electronic differentiating unit. The intracellular pulses were visualized on a two-channel oscilloscope by a microcomputer in on-line mode. The following parameters were measured: resting potential, action potential, amplitude, 50% and 90% repolarizations, maximum rate of depolarization. The preparations were stimulated through silver electrodes insulated with PTFE. Parameters of stimuli were rectangular pulses of 1 ms duration with an intensity of two times of the threshold. The basal stimulation cycles were changed between the limits of 200 msec and 1000 msec.

Those compounds which are able to prolong the duration of action potential are considered as potential antiarrhythmic agents. The effects of the compounds were examined at a concentration of 5 mg/l. According to our studies the compounds of the general formula (I) significantly prolonged the action potential duration at 90% repolarization (APD$_{90}$) but they did not change significantly the maximum rate of depolarization (V$_{max}$). Some characteristic results are shown in Table 1. Sotalol, N-{4-[1-hydroxy-2-[(1-methyl-ethyl)-amino]-ethyl]-phenyl}-methanesulphonamide, was used as reference substance.

TABLE 1

Effect of the compounds of general formula (I) on the action potential

| No. of Example | APD$_{90}$ (ms) before treatment | APD$_{90}$ (ms) after treatment | Increase of duration (%) |
|---|---|---|---|
| 1 | 259.3 ± 8.9 | 318.1 ± 10.4$^{xx}$ | 22.7 |
| 12 | 209.1 ± 6.2 | 262.2 ± 3.7$^x$ | 25.4 |
| 18 | 248.3 ± 6.5 | 307.1 ± 8.1$^{xx}$ | 23.7 |
| 22 | 221.2 ± 19.5 | 272.0 ± 22.8$^x$ | 22.9 |
| 24 | 248.4 ± 5.2 | 316.4 ± 7.5$^x$ | 27.4 |
| 26 | 246.4 ± 8.1 | 318.7 ± 13.4$^{xx}$ | 29.3 |
| 34 | 253.1 ± 11.1 | 354.6 ± 25.2$^{xx}$ | 39.9 |
| 35 | 246.5 ± 6.9 | 289.1 ± 5.3$_{xx}$ | 17.3 |
| 45 | 248.2 ± 10.4 | 329.1 ± 9.7 | 32.6 |
| 46 | 243.6 ± 16.6 | 313.6 ± 21.8 | 28.7 |
| Sotatol | 272.8 ± 4.3 | 320.0 ± 8.5$^{xx}$ | 17.3 |

$^x$ < 5%, $^{xx}$ p < 1%

The above-listed data show that the new compounds of the general formula (I) according to the invention have prolonged the action-potential duration at 90% repolarization.

II. Extracellular electrophysiologic studies on isolated rabbit heart (study of the pharmacological effect on the effective refractory period)

Young male New Zealand white rabbits, weighing 1–2 kg, were killed by a hit on the back of the head. Hearts were removed and the right ventricular walls were prepared and placed in organ bath containing Tyrode's solution. The perfusate was gassed with 95% $CO_2$. The temperature was 36°±0.5° C., pH was 7.4±0.5. After the equilibration period (60 min.) bipolar electrodes were used to stimulate the preparations. Parameters of stimuli were rectangular pulses of 2.0 ms duration with an intensity of two times of the threshold, at a cycle length of 1,000 ms.

Two bipolar extracellular platinum electrodes were positioned (d=0.1 mm) on the surface of the right ventricular wall along the trabecular fibres in order to measure impulse conduction time. The two platinum electrodes were placed in a distance of 8–12 mm from each other, then the induced biphasic extracellular action potentials were recorded. Action potentials appeared first on the nearer electrodes, then on the further electrodes; the time difference between the electrodes was considered as the impulse conduction time. The amplified signs (Experimetria GMK) were displayed in a monitor (Medicor VM 62 A). Cycle lengths were altered between 200 and 2000 ms. Measurements were carried out at the time of total adaption to the new cycle length. The threshold was measured at each new cycle length in the following way: the intensity of the stimuli was gradually decreased from the intensity of two times of the threshold until spreading action potentials were induced. The compound was applied in a concentration of 10 mg/ml. The results are summarized in Table 2.

TABLE 2

Effect of the compounds of general formula (I) on the effective refractory period (ERP)

| No. of Example | ERP (ms) before treatment | ERP (ms) after treatment |
|---|---|---|
| 1 | 116.0 ± 6.7 | 152.0 ± 3.7$^{xx}$ |
| 18 | 107.0 ± 7.6 | 136.0 ± 14.0$^x$ |
| 26 | 105.0 ± 9.5 | 127.5 ± 10.3$^x$ |
| 35 | 104.8 ± 13.2 | 135.0 ± 11.1$^{xx}$ |
| Sotalol | 86.9 ± 9.8 | 110.3 ± 9.0$^{xx}$ |

$^x$ < 5%, $^{xx}$ p < 1%

These results are similar to those obtained with intracellular electrophysiological tests and confirm the antiarrhythmic efficacy of the compounds.

The effect of the compound of Example 1 was examined in in vivo reperfusion arrhythmia model. This experiment was carried out as follows:

Anaesthetized rats weighing 400–500 g (anaesthetic: 60 mg/kg Nembutal, i.v.) were artificially ventilated. After opening the thoracic cavity the left coronary artery was pressed down (5 min. occlusion), and after cessation of the occlusion reperfusion arrhythmia (ventricular tachycardia and fibrillation) was induced which was recorded by ECG monitoring (limb lead). At the same time diastolic and systolic blood pressures were determined (invasive method: through carotid artery) and the pulse rate was also measured. Before occlusion a control electrocardiogram was recorded, and the duration of postocclusion ventricular tachycardia as well as the appearance of ventricular fibrillation were registered. Sotalol was used as reference compound. Both the test substance, compound No. 1, and the reference substance were administered in 10 mg/kg doses intravenously. The results are shown in FIG. 1.*

Figure 1:
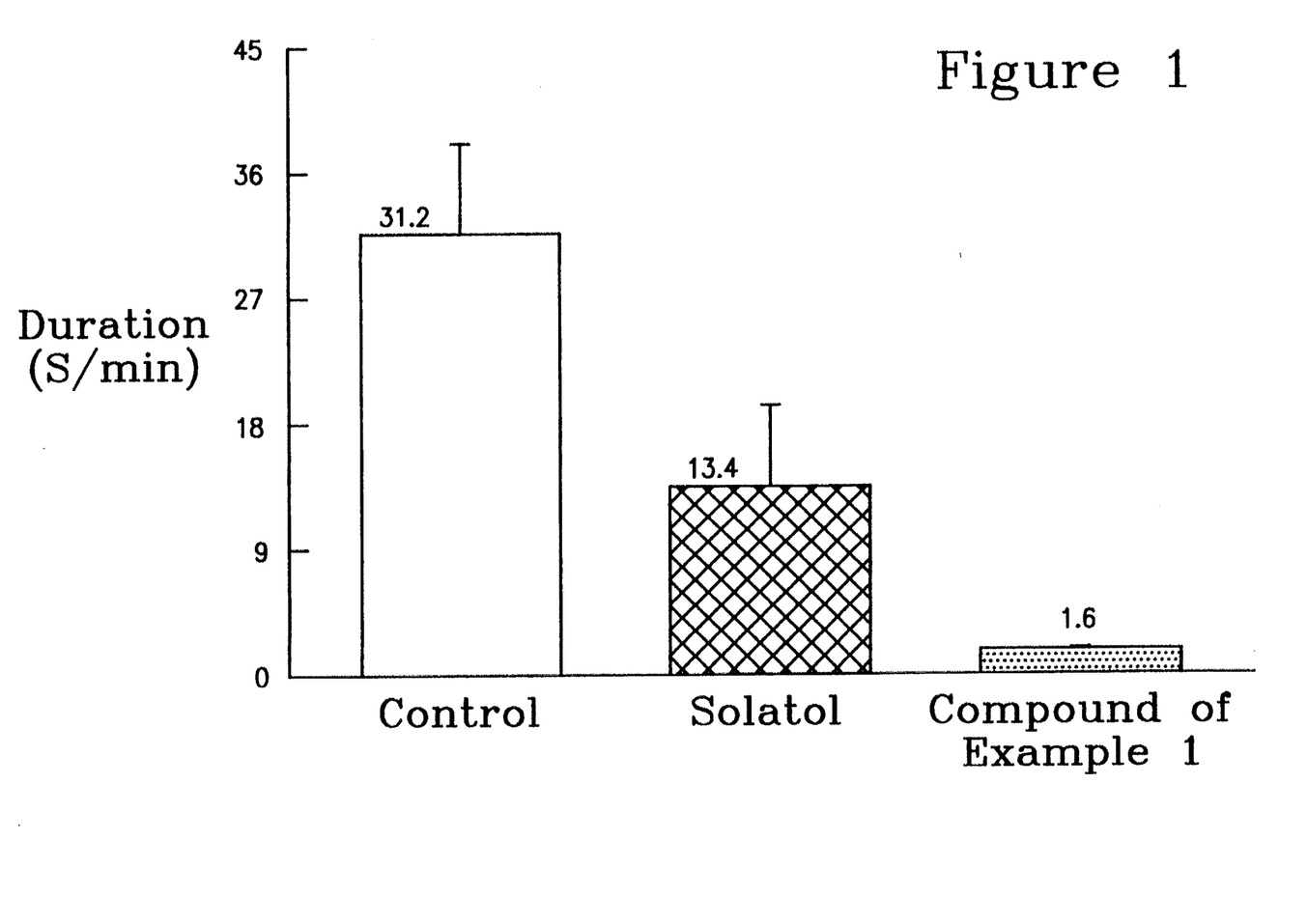

*FIG. 1 shows the average duration of ventricular tachycardia and/or ventricular fibrillation per minute.

According to the results of this experiment the compound of Example 1 appears to be considerably more effective than sotatol.

According to a further aspect of the present invention there are provided pharmaceutical compositions comprising as active ingredient a pharmaceutically effective amount of at least one racemic or optically active compound of the general formula (I), the tautomers and/or acid-addition salts thereof together with one or more pharmaceutically acceptable carrier(s), diluent(s) and/or excipient(s).

The pharmaceutical compositions of the present invention can be prepared by methods known per se by admixing the active ingredient with suitable inert solid or liquid carriers, diluents and/or excipients and bringing the mixture to galenic form.

The pharmaceutical compositions of the present invention may be suitable for oral (e.g. tablet, pill, coated pill, dragée, solid or soft gelatin capsule, solution, emulsion or suspension), parenteral (e.g. injection solution) or rectal (e.g. suppository) administration.

As carrier for the preparation of tablets, coated tablets, dragées and solid gelatin capsules e.g. lactose, corn starch, potatoe starch, talc, magnesium carbonate, magnesium stearate, calcium carbonate, stearic acid or the salts thereof, etc. can be used. As carrier for the soft gelatin capsules e.g. vegetable oils, fats, waxes or polyols of suitable consistency can be used. As carriers for the solutions and syrups e.g. water, polyols (polyethylene glycol), saccharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition, the pharmaceutical formulations may comprise auxiliaries usually applied in the pharmaceutical industry, e.g. wetting, sweetening agents, aroma substances, salts causing the change of osmotic pressure, buffers etc.

As the toxicity values of the compounds of the general formula (I) are usually low, the spectrum of activity and therapeutic reliability of the compositions according to the invention are very favourable.

The daily dose of the compounds of the general formula (I) can vary within wide ranges depending on several factors, e.g. on the activity of the active ingredient, the patient's condition and age, the severity of the disease etc. The oral daily dose is generally between 0.2 mg/kg and 25 mg/kg, preferably between 0.2 mg/kg and 10 mg/kg. It has to be stressed, however, that these dose values are only of informative character and the administered dose must always be determined by the physician therapeutist.

According to a further aspect of the present invention there is provided the use of the compounds of the general formula (I), tautomers and/or acid addition salts thereof for the preparation of pharmaceutical compositions having particularly antiarrhythmic activity.

According to a still further aspect of the present invention there is provided a method of antiarrhythmic treatment, which comprises administering to the patient an effective amount of a compound of the general formula (I), a tautomer or a pharmaceutically acceptable salt thereof.

The invention is further illustrated by the following Examples of non-limiting character. The melting points are not corrected.

EXAMPLES 1 AND 2

5-Chloro-4-{3-[N-[2-(3,4-dimethoxyphenyl)-ethyl]-N-methylamino]-propylamino}-3(2H)-pyridazinone (4-isomer) and
4-chloro-5-{3-[N-[2-(3,4-dimethoxyphenyl)-ethyl]-N-methylamino]-propylamino}-3(2H)-pyridazinone (5-isomer)

(Method $a_1$)

A solution of 3.63 g (22 mmoles) of 4,5-dichloro-3(2H)-pyridazinone and 13.88 g (55 mmoles) of N-[2-(3,4-dimethoxyphenyl)-ethyl]-N-methyl-1,3-propanediamine in 80 ml of anhydrous dioxane is boiled for 10 hours under stirring and reflux cooling. The solution is then evaporated in vacuo, the residue is subjected to chromatography on a silica gel column using as solvent mixture a 9:1:0.5 mixture of ethyl acetate, methanol and cc. ammonia. Hereinafter both the column and the thin layer chromatographic data relate to the above solvent mixture except it is specified directly. The $R_f$=0.54 fractions are combined and evaporated. Thus 2.99 g (36%) of 4-isomer melting at 92°–94° C. are obtained as the product of Example 1. The melting point of its fumarate is 94°–96° C. On going on with the chromatography using the above solvent mixture and combining and evaporating the $R_f$=0.42 fractions 4.09 g (49%) of 5-isomer are obtained as the product of Example 2. M.p.: 98°–101° C.

Its monohydrochloride salt melts at 108°–110° C.

EXAMPLES 3 AND 4

2-Benzyloxymethyl-5-chloro-4-{3-[N-[2-(3,4-dimethoxyphenyl)-ethyl]-N-methylamino]-propylamino}-3(2H)-pyridazinone (4-isomer) and
2-benzyloxymethyl-4-chloro-5-{3-[N-[2-(3,4-dimethoxyphenyl)-ethyl]-N-methylamino]-propylamino}-3(2H)-pyridazinone (5-isomer)

(Method $a_2$)

One starts from 1.2 g (4.2 mmoles) of 2-benzyloxymethyl-4,5-dichloro-3(2H)-pyridazinone (the preparation of this compound is described hereinafter under the title "Preparation of the starting substances") and 2.66 g (10.54 mmoles) of N-[2-(3,4-dimethoxyphenyl)-ethyl]-N-methyl-1,3-propanediamine and proceeds according to method $a_1$, with the difference that instead of dioxane anhydrous toluene is used and the reaction time is 5 hours. The isomers are separated according to method $a_1$. Thus 0.53 g (25%) of 4-isomer (the product of Example 3, $R_f$=0.7) and 0.87 g (41%) of 5-isomer (the product of Example 4, $R_f$=0.4) are obtained.

EXAMPLES 5 AND 6

5-chloro-4-(3-(N-(2-(3,4-dimethyoxyphenyl)-ethyl)-N-methylamino-propylamino))-2-(4-methoxybenzyl)-3(2H)-pyridazinone (4-isomer) and
4-chloro-5-(3-(N-(2-(3,4-dimethoxyphenyl)-ethyl)-N-methylamino-propylamino))-(4-methoxybenzyl)-3-(2H)-pyridazinone (5-isomer)

(Method A3)

One starts from 1.8 g (6.3 mmoles) of 4,5-dichloro-2-(4-methoxybenzyl)-3(2H)-pyridazinone and 4 g (15.8 mmoles) of N-[2-(3,4-dimethoxyphenyl)-ethyl]-N-methyl-1,3-propanediamine and proceeds according to method $A_1$, with the difference that instead of dioxane anhydrous n-butanol is used. Reaction time: 12 hours. Thus 0.85 g (27%) of 4-isomer (the product of Example 5, $R_f$=0.4, the fumarate thereof melts at 56°–57° C.) and 0.97 g (31%) of 5-isomer (the product of Example 6, $R_f$=0.2) are obtained.

EXAMPLE 7

4-Chloro-5-[1-(1,4)-diazacycloheptyl-4-(3-phenyl-2-propenyl]-3(2H)-pyridazinone (5-isomer)

(Method $a_4$)

1.65 g (10 mmoles) of 4,5-dichloro-3(2H)-pyridazinone, 21.6 g (10 mmoles) of 1-(3-phenyl-2-propenyl)-(1,4)-diazacycloheptane and 1.5 ml (11 mmoles) of triethylamine are dissolved in 16 ml of ethanol. The solution is boiled for 3 hours under stirring and reflux cooling. The mixture is then cooled, the separated product is filtered and washed with ethanol and with diethyl ether. Thus 1.83 g (53%) of the desired compound are obtained. M.p.: 176°–178° C. Its monohydrochloride salt melts at 193°–194° C.

On using appropriate starting substances and proceeding according to methods $A_1$–$A_4$ the compounds of the general formula (I) described in the following Table 3 are prepared.

TABLE 3

Structure: R¹-N-N=... pyridazinone with R²N-(CH₂)n-N(R³)(H)-CH-(CH₂)m-X-phenyl(R⁵)(R⁶), with Y on ring

| Example | Y | R¹ | R² | R³ | R⁵ | R⁶ | n | m | X | Method | Yield (%) | M.p. (°C.) or $R_f$ |
|---|---|---|---|---|---|---|---|---|---|---|---|---|
| 8 | 5-Cl | C₆H₅ | H | Me | OMe | OMe | 3 | 1 | — | A₁ | 7 | 107–113[a] |
| 9 | 4-Cl | C₆H₅ | H | Me | OMe | OMe | 3 | 1 | — | A₁ | 7 | 77–8 |
| 10 | 5-Cl | C₆H₅CH=CHCH₂ | H | Me | OMe | OMe | 3 | 1 | — | A₁ | 23 | 38–40[a] |
| 11 | 4-Cl | C₆H₅CH=CHCH₂ | H | Me | OMe | OMe | 3 | 1 | — | A₁ | 11 | 68–70[a] |
| 12 | 5-Cl | C₆H₅O(CH₂)₂N⟨piperazine⟩N(CH₂)₂ | H | Me | OMe | OMe | 3 | 1 | — | A₁ | 49 | 187–9[b] |
| 13 | 4-Cl | C₆H₅O(CH₂)₂N⟨piperazine⟩N(CH₂)₂ | H | Me | OMe | OMe | 3 | 1 | — | A₁ | 26 | 204–6[b] |
| 14 | 5-Cl | H | H | Me | OMe | OMe | 2 | 1 | — | A₁ | 26 | 102–4 |
| 15 | 4-Cl | H | H | Me | OMe | OMe | 2 | 1 | — | A₁ | 16 | 116–9 |
| 16 | 5-Cl | H | H | Me | H | H | 3 | 1 | — | A₁ | 50 | 117–9 |
| 17 | 4-Cl | H | H | Me | H | H | 3 | 1 | — | A₁ | 31 | 156–8 |
| 18 | 5-Cl | (Et)₂N(CH₂)₂ | H | Me | OMe | OMe | 3 | 1 | — | A₂ | 46 | 183–4[c] |
| 19 | 4-Cl | (Et)₂N(CH₂)₂ | H | Me | OMe | OMe | 3 | 1 | — | A₂ | 22 | 0.4[d] |
| 20 | 5-Cl | Me | H | Me | OMe | OMe | 3 | 1 | — | A₂ | 60 | 142–4[a] |
| 21 | 4-Cl | Me | H | Me | OMe | OMe | 3 | 1 | — | A₂ | 33 | 85–91 |
| 22 | 5-Cl | MeSO₂NHC₆H₄CH₂ | H | Me | OMe | OMe | 3 | 1 | — | A₂ | 45 | 125–6; 158–160[a] |
| 23 | 4-Cl | MeSO₂NHC₆H₄CH₂ | H | Me | OMe | OMe | 3 | 1 | — | A₂ | 21 | 0.56[d] |
| 24 | 5-Br | H | H | Me | OMe | OMe | 3 | 1 | — | A₂ | 41 | 95–6; 178–9[e] |
| 25 | 4-Br | H | H | Me | OMe | OMe | 3 | 1 | — | A₂ | 38 | 0.3[d] |
| 26 | 5-Cl | O⟨morpholine⟩N(CH₂)₂ | H | Me | OMe | OMe | 3 | 1 | — | A₃ | 28 | 240–2[c] |
| 27 | 4-Cl | O⟨morpholine⟩N(CH₂)₂ | H | Me | OMe | OMe | 3 | 1 | — | A₃ | 47 | 73 |
| 28 | 5-Cl | C₆H₅CH=CHCH₂N⟨piperazine⟩N(CH₂)₂ | H | Me | OMe | OMe | 3 | 1 | — | A₃ | 25 | 182–6[f] |
| 29 | 4-Cl | C₆H₅CH=CHCH₂N⟨piperazine⟩N(CH₂)₂ | H | Me | OMe | OMe | 3 | 1 | — | A₃ | 33 | 217–221[f] |
| 30 | 4-Cl | (Et)₂N(CH₂)₂ | CH₂—CH₂ | H | NHSO₂Me | | 2 | 1 | O | A₄ | 38 | 146–7 |
| 31 | 4-Cl | O⟨morpholine⟩N(CH₂)₂ | CH₂—CH₂ | H | H | | 2 | 0 | CH=CH | A₄ | 8,5 | 225–6[c] |
| 32 | 4-Cl | (Et)₂N(CH₂)₂ | CH₂—CH₂—CH₂ | H | H | H | 2 | 0 | CH=CH | A₄ | 67 | 0.46[d] |
| 33 | 4-Cl | H | CH₂—CH₂ | H | H | | 2 | 1 | O | A₄ | 44 | 149–150 |
| 34 | 4-Cl | H | CH₂—CH₂ | H | H | | 2 | 0 | CH=CH | A₄ | 74 | 209–211; |

TABLE 3-continued

| Example | Y | R¹ | R² | R³ | R⁵ | R⁶ | n | m | X | Method | Yield (%) | M.p. (°C.) or R$_f$ |
|---|---|---|---|---|---|---|---|---|---|---|---|---|
| 35 | 4-Cl | (Et)₂N(CH₂)₂ | CH₂—CH₂ | | H | H | 2 | 0 | CH=CH | A4 | 44 | 158–160$^e$ decomposition 87–9; 221–3$^c$ |
| 36 | 5-Cl | (Et)₂N(CH₂)₂ | CH₂—CH₂ | | H | H | 2 | 0 | CH=CH | A4 | 21 | 212–14$^c$ |
| 37 | 4-Cl | (Et)₂N(CH₂)₂ | CH₂—CH₂ | | H | F | 2 | 0 | CH=CH | A4 | 32 | 174–5 |
| 38 | 5-Cl | (Et)₂N(CH₂)₂ | CH₂—CH₂ | | H | F | 2 | 0 | CH=CH | A4 | 10 | 0.75$^d$ |

$^a$fumarate
$^b$3HCl.2H₂O salt
$^c$HCl salt
$^d$R$_f$(EtOAc:MeOH:ccNH₃ = 9:1:0,5).
$^e$HCl salt
$^f$3HCl salt If desired, the isomeric forms of the compounds of Examples 31, 32, 36 and 38 are separated by evaporating the reaction mixture and subjecting the residue to column chromatography.

EXAMPLE 39

4-Chloro-5-{3-[N-[2-(3,4-dimethoxyphenyl)-ethyl]-N-methylamino]-propylamino}-2-[3-(4-fluorophenyl)-2-propenyl-3(2H)-pyridazinone (Method b)

To a suspension of 5.7 g (15 mmoles) of 4-chloro-5-{3-[N-[2-(3,4-dimethoxyphenyl)-ethyl]-N-methylamino]-propylamino}-3(2H)-pyridazinone (prepared according to Example 2) and 10.2 g (74 mmoles) of anhydrous potassium carbonate in 15 ml of anhydrous dimethylformamide a solution of 2.73 g (16 mmoles) of 3-(4-fluorophenyl)-2-propenyl chloride in 3 ml of anhydrous dimethylformamide is dropped under stirring, while the inner temperature is kept at 10°–15° C. The reaction mixture is stirred at room temperature for a day. The dimethylformamid is then evaporated in vacuo, a slight amount of water is added to the residue and the emulsion thus obtained is extracted with ethyl acetate. The organic phase is dried and evaporated, then the residue is crystallized from diethyl ether. Thus 3.24 g (42%) of the desired compound are obtained. M.p.: 84°–85° C.

EXAMPLE 40

5-Chloro-4-{3-[N-[2-(3,4-dimethoxyphenyl)-ethyl]-N-methylamino]-propylamino}-2-[3-(4-fluorophenyl)-2-propenyl]-3(2H)-pyridazinone On starting from the compound of Example 1 and proceeding according to method B the aimed compound is obtained with a yield of 39%. R$_f$=0.5 (EtOAc-MeOH=9:1), its monohydrochloride salt melts at 126°–127° C.

EXAMPLE 41

5Chloro-2-methyl-4-{3-[N-(3-phenyl-2-propyl)-N-methylamino]-propylamino}-3(2H)-pyridazinone (Method c)

A mixture of 1.77 g (7.5 moles) of 5-chloro-4-(3-chloropropylamino)-2-methyl-3(2H)-pyridazinone prepared as described hereinafter under the title "Preparation of the starting substances" and 3.73 g (25 mmoles) of N,α-dimethylphenyl ethyl amine is melted at a temperature of 120° C. for 5 hours. Then it is cooled, 20 ml of water are added and the solution is extracted with ethyl acetate. The extract is cooled and evaporated and the crude product is purified by column chromatography. Thus 1.67 g (64%) of the aimed compound are obtained. R$_f$=0.5. Its fumarate salt melts at 128°–129° C.

EXAMPLE 42

5Chloro-2-methyl-4-{3-[N-[2-(3,4,5-trimethoxyphenyl)-ethyl]-N-methylamino]-propylamino}-3(2H)-pyridazinone On starting from 5-chloro-4-(3-chloropropylamino)-2-methyl-3(2H)-pyridazinone and 3,4,5-trimethoxyphenyl ethyl amine and proceeding according to method c) with the difference that melting is carried out at 140° C. for 2.5 hours the desired compound is obtained with a yield of 34%. R$_f$=0.6.

EXAMPLE 43

4-Chloro-2-methyl-5-[4-(3-phenyl-2-propenyl)-1-piperazinyl]-3(2H)-pyridazinone (Method d₁)

0.75 g (3.3 mmoles) of 4-chloro-2-methyl-5-(1-piperazinyl)-3(2H)-pyridazinone prepared as described hereinafter under the title "Preparation of the starting substances" and 0.91 g (6.6 mmoles) of anhydrous potassium carbonate are suspended in 5 ml of anhydrous dimethyl formamide. Then a solution of 0.5 g (3.3 moles) of 3-phenyl-2-propenyl chloride in 5 ml of anhydrous dimethyl formamide are dropped to the suspension, and the reaction mixture is stirred at room temperature for 24 hours. The dimethyl formamide is evaporated in vacuo, a slight amount of water is added to the residue and the solution thus obtained is extracted with ethyl acetate. The organic phase is dried and evaporated and the residue is crystallized from ethanol. Thus 0.55 g (49%) of the desired compound is obtained. M.p.: 98°–100° C. Its monohydrochloride salt melts at 218°–220° C.

EXAMPLE 44

2-Benzyloxymethyl-5-chloro-4-{3-[N-[2-[4-[(methylsulfonyl)-amino]-phenoxy]-ethyl]-N-methylamino]-propylamino}-3(2H)-pyridazinone (Method $d_2$)

A mixture of 3.2 g (9.5 mmoles) of 2-benzyloxymethyl-5-chloro-4-[3-(N-methylamino)-propylamino]-3(2H)-pyridazinone, 3.56 g (14.25 mmoles) of 4-[(methylsulfonyl)-amino]-phenoxyethyl chloride and 2 ml (14.25 mmoles) of triethylamine is melted at a temperature of 80° C. for 16 hours. Then it is subjected to column chromatography using first ethyl acetate, then a 9:1:0.5 mixture of ethyl acetate—methanol—cc. ammonia. Thus 1.8 g (69%) of the aimed compound are obtained. $R_f$=0.7.

EXAMPLE 45

5Chloro-4-{3-[N-[2-[4-[(methylsulfonyl)-amino]-phenoxy]-ethyl]-N-methylamino]-propylamino}-3(2H)-pyridazinone (Method e)

2.69 g (4.88 mmoles) of the compound of Example 44 are dissolved in 53 ml of anhydrous benzene. 2.92 ml of boron tribromide are dropped to the solution so that the temperature of the reaction mixture should not exceed 20° C. The suspension thus obtained is stirred at room temperature for half an hour. Then 40 ml of methanol are dropped under stirring and cooling with icy water at such a rate that the inner temperature should not exceed 25° C. The reaction mixture is evaporated, the residue is boiled with 68 ml of distilled water for 1 hour, the solution is cooled, diluted with 100 ml of distilled water, the pH is adjusted with solid potassium hydrogen carbonate to neutral and the solution is extracted with chloroform. The organic phase is dried and evaporated, then the residue is purified by column chromatography. Thus 1.01 g (48%) of the desired compound are obtained. $R_f$=0.45. Its monohydrochloride salt melts at 181°–183° C.

EXAMPLE 46

4-{3-[N-[2-(3,4-Dimethoxyphenyl)-ethyl]-N-methylamino]-propylamino}-3(2H)-pyridazinone dihydrochloride (Method f)

0.52 g (1.36 mmole) of 5-chloro-4-{3-[N-[2-(3,4-dimethoxyphenyl)-ethyl]-N-methylamino]-propylamino}-3(2H)-pyridazinone prepared according to Example 1 is dissolved in a mixture of 20 ml of ethanol and 1.25 ml of cc. ammonium hydroxide. The solution is subjected to hydrogenation under atmospheric pressure, in the presence of 0.3 g of 10% palladium charcoal catalyst, using a Paar equipment. When the desired hydrogen uptake has been achieved, the catalyst is filtered off and the filtrate is evaporated. The residue is dissolved in a slight amount of dichloromethane and the solution is filtered.

The clean solution is evaporated, the residue is dissolved in 3 ml of ethanol, and the solution thus obtained is adjusted to pH=2 with a solution of anhydrous hydrogen chloride gas in ethanol under stirring and ice-cooling. The solution is allowed to stand overnight at −10° C., then the separated crystals are filtered, washed and dried. Thus 0.42 g (74%) of the desired compound is obtained. M.p.: 169°–171° C.

On starting from appropriate starting substances and proceeding according to method f) further compounds enumerated in the following Table 4 are prepared:

TABLE 4

$R^1\!-\!N\!-\!$(pyridazinone ring)$-NH-(CH_2)_3-N(CH_3)-(CH_2)_2-$(phenyl-OMe, OMe)

| Example | $R^1$ | Method | Yield (%) | M.p. (°C.) |
|---|---|---|---|---|
| 47 | O(CH₂CH₂)₂N/CH₂/2 | f | 62 | 228–30$^a$ |
| 48 | /Et/₂N/CH₂/2 | f | 70 | 130–34$^a$ |
| 49 | PhO/CH₂/2N(CH₂CH₂)₂N/CH₂/2 | f | 56 | 157–59$^b$ |

$^a$2HCl.H₂O;
$^b$3HCl.2H₂O

Preparation of acid addition salts

5-Chloro-4-{3-[N-(2-phenylethyl)-N-methylamino]-propylamino-3(2H) -pyridazinone fumarate To a solution of 0.9 g (2.8 mmoles) of the base of Example 14 in 8 ml of ethanol a solution of 0.33 g (2.8 moles) of fumaric acid in 6 ml of ethanol of 70° C. prepared at a temperature of 70° C is dropped at the same temperature, under stirring. The mixture is allowed to stand overnight at −10° C., the separated crystals are filtered off, washed and dried. Thus 1.01 g (83%) of the desired compound are obtained. M.p.: 164°–167° C.

4-Chloro-2-[2-(N,N-diethylamino)-ethyl]-5-{4-[(2-[4-[(methylsulfonyl)-amino]-phenoxy]-ethyl]-1-piperazinyl}-3(2H)-pyridazinone dihydrochloride A suspension of 0.8 g (1.5 mmoles) of the base of Example 30 in 11 ml of anhydrous acetone is adjusted to pH 2 by introducing anhydrous hydrogen chloride gas under stirring and ice-cooling. The solution is allowed to stand overnight at −10° C., then the separated crystals are filtered off, washed and dried. Thus 0.82 g (91%) of the desired compound is obtained. M.p.: 171°–173° C.

Preparation of the starting substances

1. The new 4,5-dihalo-3(2H)-pyridazinones of the general formula (III) can be prepared according to the following methods:

Method i)

4,5-Dichloro-a-{a-[4-(2-phenoxyethyl)-1-piperazinyl]-ethyl}-3(2H)-pyridazinone dihydrochloride To a solution of 0.69 g (30 mmoles) of sodium metal in 20 ml of anhydrous ethanol 1.65 g (10 mmoles) of 4,5-dichloro-3(2H)-pyridazinone are added at room temperature under stirring. The mixture is stirred for 15 minutes, then 3.41 g (10 mmoles) of 2-[4-(2-phenoxyethyl)-1-piperazinyl]-ethyl chloride dihydrochloride are added, and the reaction mixture is boiled for 2 hours under stirring and reflux cooling. The separated sodium chloride is filtered and the filtrate is converted into salt with a solution of anhydrous hydrogen chloride gas in ethanol. Yield: 73%, m.p.: 208°–210° C.

4,5-Dichloro-2-{2-[4-(3-phenyl-2-propenyl)-1-piperazinyl]-ethyl}-3(2H)-pyridazinone dihydrochloride On proceeding according to the above method but using an appropriately substituted alkyl chloride the desired compound is obtained with a yield of 66%. M.p.: 238°–240° C.

Method ii)

4,5-Dichloro-2-(4-methoxybenzyl)-3(2H)-pyridazinone 1.65 g (10 mmoles) of 4,5-dichloro-3(2H)-pyridazinone are converted into potassium salt with an equimolar amount of potassium hydroxide dissolved in methanol, and the methanol is removed in vacuo. To the suspension of the salt in 30 ml of toluene a solution of 1.56 g (10 mmoles) of 4-methoxybenzyl chloride in 30 ml of toluene is dropped under stirring, then 0.6 g (1.8 mmole) of tetrabutyl ammonium bromide is added. The reaction mixture is boiled for 3 hours under reflux cooling and evaporated to dryness in vacuo. The residue is dissolved in water, then the solution is extracted with ethyl acetate, dried and evaporated. The crude product thus obtained is optionally subjected to column chromatography on a silica gel column using ethyl acetate as solvent. Thus 1.17 g (41%) of the desired compound are obtained. M.p.: 117°–120° C.

2-Benzyloxymethyl-4,5-dichloro-3(2H)-pyridazinone

On proceeding according to the above method but using benzyloxymethyl chloride instead of 4-methoxybenzyl chloride the desired compound is obtained with a yield of 60%. M.p.: 60°–64° C.

Method iii)

4,5-Dichloro-2-(3-phenyl-2-propenyl)-3(2H)-pyridazinone

To a suspension of 16.5 g (100 mmoles) of 4,5-dichloro-3(2H)-pyridazinone and 150 g (163 mmoles) of anhydrous potassium carbonate in 100 ml of anhydrous dimethylformamide a solution of 16.8 g (110 mmoles) of 3-phenyl-2-propenyl chloride in 5 ml of anhydrous dimethylformamide is dropped under stirring and cooling at a temperature below 15° C. The reaction mixture is stirred at room temperature for a day and poured onto 600 ml of water under stirring. The separated crystals are filtered, washed with water, dried and optionally purified by treating with aluminium oxide in a benzene solution. Thus 24.9 g (89%) of the desired compound are obtained. M.p.: 98°–99° C.

Method iv)

4,5-Dichloro-2-{4-[(methylsulfonyl)-amino]-benzyl}-3(2H)-pyridazinone 4.5 g (15 mmoles) of 4,5-dichloro-2-(4-nitrobenzyl)-3(2H)-pyridazinone (prepared according to method III but using 4-nitrobenzyl chloride instead of 3-phenyl-2-propenyl chloride (M.P. 128–130 celsius)) are dissolved in 150 ml of 99.5% acetic acid solution. Then 7.5 g of iron dust are added to the solution at such a rate that the temperature should not exceed 20° C., and the suspension is stirred at room temperature for 8 hours. By working up the reaction mixture in the usual manner 3.15 g (77%) of 2-(4-aminobenzyl)-4,5-dichloro-3(2H)-pyridazinone melting at 187°–189° C. are obtained, which is dissolved in 34 ml of anhydrous pyridine. To the solution 1.24 ml (16 moles) of methanesulfonyl chloride are dropped under stirring and cooling at such a rate that the inner temperature should remain between 0° C. and 5° C. The mixture is then stirred at room temperature for 4 hours and poured onto water. The separated crystals are filtered and washed with water. Thus 2.34 g (57%) of the desired compound are obtained. M.p.: 152°–154° C.

2. The new 1-substituted piperazines and 1-substituted (1,4)-diazacycloheptanes of the general formula (IV) can be prepared according to the following methods:

Method i)

1-[3-(4-Fluorophenyl)-2-propenyl]-piperazine

To a boiling solution of 32.4 g (376 mmoles) of anhydrous piperazine in 45 ml of anhydrous ethanol a solution of 6.3 g (37 mmoles) of 3-(4-fluorophenyl)-2-propenyl chloride in 60 ml of anhydrous ethanol is dropped under stirring and reflux cooling, within 1 hour. The solvent is removed in vacuo, the residue is dissolved in chloroform and washed with water to be free from piperazine. The organic phase is dried, evaporated and the crude product is—if necessary—distilled off in vacuo. Thus 5.4 g (66%) of the desired compound are obtained. B.p.: 148° C./80 Pa.

1-(3-Phenyl-2-propenyl)-(1,4)-diazacycloheptane

On proceeding according to the above method but using 1,4-diazacycloheptane instead of piperazine and 3-phenyl-2-propenyl chloride instead of 3-(4-fluorophenyl)-2-propenyl chloride the desired compound is obtained with a yield of 91%. $R_f$=0.25.

1-{2-[4-[(Methylsulfonyl)-amino]-phenoxy]-ethyl}-piperazine monohydrate

On proceeding according to the above method but using 2-{4-[(methylsulfonyl)-amino]-phenoxy}-ethyl chloride instead of 3-(4-fluorophenyl)-2-propenyl chloride the desired compound is obtained with a yield of 40%. M.p.: 212°–214° C.

3. The new 3(2H)-pyridazinones of the general formula (V) can be prepared e.g. according to the following methods:

Method i)

5Chloro-4-[N-(3-hydroxypropyl)-amino]-2-methyl-3(2H)-pyridazinone 3.58 g (20 mmoles) of 4,5-dichloro-2-methyl-3(2H)-pyridazinone and 3.76 g (50 mmoles) of 3-aminopropanol are dissolved in 35 ml of water. The mixture is boiled for 4 hours under stirring and reflux cooling, then it is cooled and extracted with 200 ml of dichloromethane. The organic phase is dried, evaporated and the crude product is subjected to chromatography on a silica gel column. Thus 0.84 g (19%) of the desired compound is obtained. M.p.: 65°–66° C., $R_f$=0.7.

2-Benzyloxymethyl-5-chloro-4-[N-(3-hydroxypropyl)-amino]-3(2H)-pyridazinone can also be produced according to the above method. In this case 2-benzyloxymethyl-4,5-dichloro-3(2H)-pyridazinone is used as starting substance Yield: 28%, $R_f$=0.75, m.p.: 54°–56° C.

Method ii)

5Chloro-4-[N-(3-chloropropyl)-amino]-2-methyl-3(2H)-pyridazinone 0.48 g (2.2 mmoles) of 5-chloro-4-[N-(3-hydroxypropyl)-amino]-2-methyl-3(2H)-pyridazinone is dissolved in ml of dichloromethane, and 2.1 ml (28.8 mmoles) of thionyl chloride are dropped to the solution. Then it is boiled for 3 hours under stirring and reflux cooling. The solvent is evaporated and the crude product thus obtained is triturated with ether. Thus 0.38 g (73%) of the desired compound is obtained. M.p.: 91°–92° C.

2-Benzyloxymethyl-5-chloro-4-[N-(3-chloropropyl)-amino]-3(2H)-pyridazinone can also be prepared according to the above method by using appropriate starting substances. Yield: 70%. M.p.: 42°–46° C.

4. The new 3(2H)-pyridazinones of the general formula (VIII) can be prepared e.g. according to the following methods:

Method i)

4-Chloro-2-methyl-5-(1-piperazinyl)-3(2H)-pyridazinone

A solution of 4.48 g (25 mmoles) of 4,5-dichloro-2-methyl-3(2H)-pyridazinone and 17.2 g (200 mmoles) of piperazine in 45 ml of anhydrous ethanol is boiled for 4 hours under stirring and reflux cooling. The solvent is evaporated in vacuo and the residue is dissolved in a mixture of water and dichloromethane. The organic phase is washed with water, dried and evaporated. The residue is triturated with ether. Thus 3.44 g (60%) of the desired compound are obtained. M.p.: 83°–87° C.

Method ii)

2-Benzyloxymethyl-5-chloro-4-{N-[3-(methylamino)-propyl]-amino}-3(2H)-pyridazinone 5.35 g (15.63 mmoles) of 2-benzyloxymethyl-5-chloro-4-[N-(3-chloropropyl)-amino]-3(2H)-pyridazinone [which can be prepared according to method 3.ii)] are dissolved in 40 ml of ethanol containing 33% of methylamine. The solution is kept at 100° C. for 5 hours in a pressure-tight steel tube. The solvent is evaporated and the residue is subjected to chromatography on a silica gel column. Thus 4.19 g (80%) of the desired compound are obtained. $R_f=0.35$.

What we claim is:

1. A racemic or optically active 3(2H)-pyridazinone which is
   5-chloro-2-(2-(N,N-diethylamino)-ethyl)-4-(3-(N-(2-(3,4-dimethoxyphenyl)-ethyl)-N-methylamino)-propylamino)-3(2H)-pyridazinone,
   5-chloro-4-(3-(N-(2-(3,4-dimethoxyphenyl)-ethyl)-N-methylamino)-propylamino)-2-(4-((methylsulfonyl)-amino)-benzyl)-3-(2H)-pyridazinone, or
   5-chloro-4-(3-(N-(2-(4-((methylsulfonyl)-amino)-phenoxy)-ethyl)-N-methylamino)-propylamino)-3(2H)-pyridazinone.

2. The 3(2H)-pyridazinone according to claim 1 which is 5-chloro-2-(2-(N,N-diethylamino)-ethyl)-4-(3-(N-(2-(3,4-dimethoxyphenyl)-ethyl)-N-methylamino)-propylamino)-3(2H)-pyridazinone.

3. The 3(2H)-pyridazinone according to claim 1 which is 5-chloro-4-(3-(N-(2-(3,4-dimethoxyphenyl)-ethyl)-N-methylamino)-propylamino)-2-(4-((methylsulfonyl)-amino)-benzyl)-3(2H)-pyridazinone.

4. The 3(2H)-pyridazinone according to claim 1 which is 5-chloro-4-(3-(N-(2-(4-((methylsulfonyl)-amino)-phenoxy)-ethyl)-N-methylamino)-propylamino)-3(2H)-pyridazinone.

5. A racemic or optically active 3(2H)-pyridazinone which is 5-chloro-4-(3-(N-(2-(3,4-dimethoxyphenyl)-ethyl)-N-methylamino)-propylamino)-3(2H)-pyridazinone.

* * * * *